US 6,585,696 B2

(12) United States Patent
Petersen et al.

(10) Patent No.: US 6,585,696 B2
(45) Date of Patent: Jul. 1, 2003

(54) METHOD AND APPARATUS FOR APPLYING A MEDICALLY USEFUL MULTIPLE COMPONENT MATERIAL

(75) Inventors: Robert L. Petersen, Winthrop Harbor, IL (US); James C. Laird, Grayslake, IL (US); Jorge Delcastillo, Des Plaines, IL (US); Jacquelynn Welter, Bristol, WI (US); Atif M. Yardimci, Northbrook, IL (US)

(73) Assignee: Baxter International, Inc., Deerfield, IL (US)

( * ) Notice: Subject to any disclaimer, the term of this patent is extended or adjusted under 35 U.S.C. 154(b) by 31 days.

(21) Appl. No.: 09/746,210

(22) Filed: Dec. 22, 2000

(65) Prior Publication Data

US 2002/0082563 A1 Jun. 27, 2002

(51) Int. Cl.[7] .................................. A61M 5/00
(52) U.S. Cl. .................... 604/191; 604/210; 604/82; 222/391
(58) Field of Search .................... 604/82, 191, 187, 604/210; 222/137, 391

(56) References Cited

U.S. PATENT DOCUMENTS

| | | | |
|---|---|---|---|
| 1,595,424 A | 8/1926 | Sather | |
| 3,223,083 A | 12/1965 | Cobey | |
| 3,517,668 A | 6/1970 | Brickson | |
| 3,905,365 A | 9/1975 | Colombo | |
| 4,359,049 A | 11/1982 | Redl et al. | |
| 4,364,388 A | 12/1982 | Cech | |
| 4,452,285 A | 6/1984 | Leibhard et al. | |
| 4,526,303 A | 7/1985 | Harrod | |
| 4,566,610 A | 1/1986 | Herb | |
| 4,581,022 A | 4/1986 | Leonard et al. | |
| 4,655,372 A | 4/1987 | Ross et al. | |
| 4,666,429 A | 5/1987 | Stone | |
| 4,690,306 A | 9/1987 | Stäheli | |
| 4,710,178 A | 12/1987 | Leonard | |
| 4,784,157 A | 11/1988 | Halls | |
| 4,795,441 A | 1/1989 | Bhatt | |
| 4,902,281 A | 2/1990 | Avoy | |
| 4,934,827 A | 6/1990 | Taschke et al. | |
| 4,994,065 A | 2/1991 | Gibbs et al. | |
| 5,065,906 A | 11/1991 | Maeder | |
| 5,116,315 A | * 5/1992 | Capozzi et al. | ............. 222/137 |
| 5,376,079 A | 12/1994 | Holm | |

(List continued on next page.)

FOREIGN PATENT DOCUMENTS

| | | |
|---|---|---|
| CA | 2000659 | 4/1990 |
| CA | 2021044 | 1/1991 |
| DE | 3234250 | 3/1984 |
| DE | 3602975 | 8/1987 |
| DE | 3930315 | 8/1989 |
| DE | 3920694 | 1/1991 |
| EP | 0054156 | 6/1982 |
| EP | 0109913 | 5/1984 |
| EP | 0363967 | 4/1990 |
| EP | 0408494 | 1/1991 |
| WO | 8704645 | 8/1987 |
| WO | 8802259 | 4/1988 |
| WO | 9306940 | 4/1993 |
| WO | 9813094 | 4/1998 |
| WO | 9917833 | 4/1999 |
| WO | 9917834 | 4/1999 |
| WO | 9944672 | 9/1999 |
| WO | 0053339 | 9/2000 |

*Primary Examiner*—Erick Solis
(74) *Attorney, Agent, or Firm*—Oppenheimer Wolff & Donnelly (57) ABSTRACT

An applicator gun for spraying a medically useful multiple component fluid to an area of interest. The handheld applicator gun functionally receives a commercially available or standardized multi-syringe applicator, and dispenses fluid from the multi-syringe applicator in a controllable manner. The handheld applicator gun further includes a return stop and a dispensing stop to limit the force exerted on the multi-syringe applicator.

35 Claims, 8 Drawing Sheets

U.S. PATENT DOCUMENTS

| | | |
|---|---|---|
| 5,520,658 A | 5/1996 | Holm |
| 5,535,922 A * | 7/1996 | Maziarz .................. 222/137 |
| 5,664,701 A | 9/1997 | Massena |
| 5,722,829 A | 3/1998 | Wilcox et al. |
| 5,749,968 A | 5/1998 | Melanson et al. |
| 5,755,362 A | 5/1998 | Rodriguez, Jr. et al. |
| 5,759,169 A | 6/1998 | Marx |
| 5,759,171 A | 6/1998 | Coelho et al. |
| 5,769,272 A | 6/1998 | Massena |
| 5,779,103 A | 7/1998 | Massena |
| 5,951,531 A | 9/1999 | Ferdman et al. |
| 5,975,367 A | 11/1999 | Coelho et al. |
| 5,992,694 A | 11/1999 | Keller |
| 6,007,515 A | 12/1999 | Epstein et al. |
| 6,047,861 A | 4/2000 | Vidal et al. |
| 6,059,749 A | 5/2000 | Marx |
| 6,165,201 A | 12/2000 | Sawhney et al. |
| 6,213,984 B1 * | 4/2001 | Lane et al. .................. 604/207 |

* cited by examiner

METHOD AND APPARATUS FOR APPLYING A MEDICALLY USEFUL MULTIPLE COMPONENT MATERIAL

BACKGROUND OF THE INVENTION

Use of tissue sealants and other biological materials is an important emerging surgical technique, well adapted for the operating room or field environments such as the doctor's office or mobile medical units. Preferred sealants include fibrin sealants which are formed from blood plasma components and comprise, on the one hand, a first component containing fibrinogen and Factor XIII and, on the other hand, a second component which usually includes thrombin, and calcium ions, however, other formulations may exist. The fibrinogen is capable of a polymerizing and being cross-linked to form a solid fibrin clot when the components are mixed. The necessary additional factors to simulate relevant portions of the natural blood coagulation cascade are suitably distributed between the fibrinogen and thrombin components.

Depending upon the potency of the particular formulations employed, coagulation of the sealant may take place very rapidly, yielding a gel within perhaps 10 or 20 seconds. Though often very desirable for surgical reasons, such fast-acting properties present potential problems of fouling or clogging. These problems must be overcome in devising suitable applicators, methods of application, and devices suitable for filling said applicators.

U.S. Pat. No. 5,585,007, issued to Antanavich et al., whose disclosure and references are hereby incorporated herein by reference thereto, provides an extensive discussion of the literature relating to fibrinogen sealant preparation (column 1, line 20 to column 4, line 62) and applicators column 4 line 62 to column 5, line 14), as well as a bibliography, (columns 6–10) and is a helpful guide to the teachings of prior workers in the field.

Until May of 1998, when the FDA first approved such products, fibrin sealant was not commercially available in the US. Therefore, use of fibrin sealant was limited to supplies produced within a clinic, and not subject to FDA control. After FDA approval, however, fibrin sealant became commercially available in the US. This availability has created a need for an effective and efficient device useful for dispensing the components of the sealant from commercially available or standardized applicators to an area of interest in a controlled, efficient manner.

A popular manually operable applicator for such two-component sealants employs a dual syringe construction wherein two syringes, connected by a yoke, each provide a reservoir for one of the components. In most prior devices, the sealant components are discharged in separate streams and mixed externally of the applicator. Such applicators are similar in principle to household epoxy glue applicators commonly available in hardware stores. While the syringe-type applicators have proved beneficial when applying a multiple component sealant, use of these applicators occasionally resulted in fatigue of the operator's hand.

Thus, there is a need for an easy to operate device capable of applying a multiple component fluid from a multi-syringe applicator to an area of interest.

SUMMARY OF THE INVENTION

The present invention solves the problem of effectively delivering multiple components directly from commercially available or standardized applicators, for example, multi-syringe applicators, to an area of interest. Additionally, the present invention provides increased dispensing control while enhancing operator comfort.

In one aspect, the present invention provides a multi-component applicator comprising a multi-syringe applicator and a handheld applicator adapted to functionally receive a multi-syringe applicator and dispense material stored in the multi-syringe applicator.

The multi-syringe applicator has a first syringe container and a second syringe container. The first syringe container, storing a first component, comprises a first syringe piston, a portion of which is slidably positioned within the first syringe container, a first piston rod attached thereto, and a first syringe pusher attached to the first piston rod. Likewise, the second syringe container, storing a second component, comprises a second piston, a portion of which is slidably positioned within the second syringe container, a second piston rod attached thereto, and a second syringe pusher attached to the second piston rod.

The handheld applicator comprises an applicator housing having an elongated body portion, a stationary handle portion, and a moveable trigger device. Located within the applicator housing is an applicator cavity containing an engagement member and a movement actuator. The engagement member and the movement actuator functionally couple the motion of the moveable trigger device to the dispensing action of the handheld applicator.

Also positioned within the applicator cavity is a return stop and a dispensing stop. These stops regulate the amount of force applied by the handheld applicator to the multi-syringe applicator. It has been shown that multi-syringe applicators have an optimal range of force that may be applied to the syringes to achieve the desired dispensing effect. Normally, the application of insufficient force by the handheld applicator results in the components being dispensed in inadequate or uneven flowrates, or the material being dispensed in a liquid stream. The application of excessive force by the handheld applicator results in insufficient component mixing, and may, in extreme cases, result in failure of the multi-syringe applicator, or the handheld applicator, or both. The present invention addresses and solves this problem by utilizing a return stop and a dispensing stop. The return stop limits the stroke length of the moveable trigger device by providing a physical stop which contacts the moveable trigger device and limits the obtainable sweep length of the moveable trigger device with regard to the stationary handle. The dispensing stop limits the amount the engagement device will advance during each operational cycle. The return stop and dispensing stop effectively regulate the mechanical advantage the handheld applicator may apply to the multi-syringe applicator during one operational cycle.

The distal portion of the handheld applicator may be capable of receiving a plurality of dispensing tips. For example, in one embodiment the distal portion of the handheld applicator may dispose a detachable spray tip, which mixes and atomizes the various components just prior to application. The present invention may dispense the material in a plurality of manners, including, without limitation, liquid stream form and spray form.

In an additional embodiment of the present invention, a force dampener is positioned at the interface between the handheld applicator and the multi-syringe applicator. The force dampener prevents damage to the multi-syringe applicator and provides an additional force limiting function.

Other objects and further features of the present invention will become apparent from the following detailed description when read in conjunction with the attached drawings.

DETAILED DESCRIPTION OF THE DRAWINGS

Disclosed herein is a detailed description of various illustrated embodiments of the present invention. This description is not to be taken in a limiting sense, but is made merely for the purpose of illustrating the general principles of the invention.

The applicator device of the present invention is used to facilitate the application of medically useful multiple component fluids. More particularly, the present invention enables the operator to easily apply material from commercially available component dispensers with an increased degree of controllability. In addition to increasing control, the present invention greatly enhances operator comfort. As those skilled in the art will appreciate, the present invention is simple and inexpensive to manufacture and utilizes existing handheld multiple-syringe applicators, such as, for example, the Duploject™ Applicator manufactured by the Baxter Corporation. It is anticipated as being within the scope of the present invention to produce a handheld applicator capable of functionally coupling with a plurality of multi-syringe applicators in a plurality of sizes.

Figure 1:
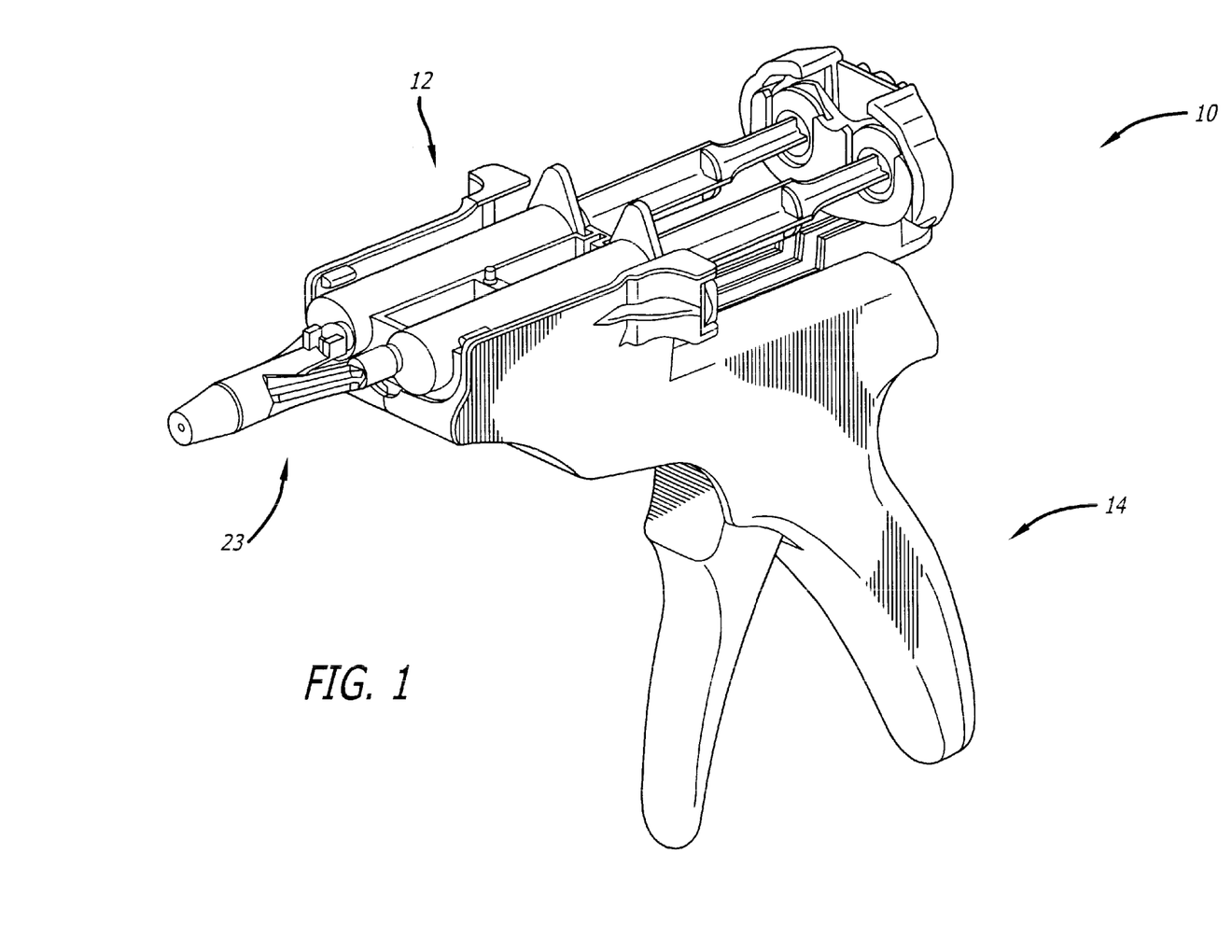
FIG. 1 is an elevated view of the multi-syringe applicator and hand held applicator of the present invention.

FIG. 1 shows an apparatus 10 for controllably dispensing and applying a medically useful multiple component material. The apparatus 10 includes a multi-syringe applicator 12 and a handheld applicator 14. As those skilled in the art of ergonomics will appreciate, the relative size and physical characteristics of the handheld applicator 14 enhance user comfort when compared with a multi-syringe applicator 12. Attached to the distal portion of the multi-syringe applicator is a spray dispensing tip 23. The apparatus 10 may be operated without the spray dispensing tip 23, and may be coupled to a plurality of alternative dispensing devices, including multi-lumen catheters.

Figure 2:
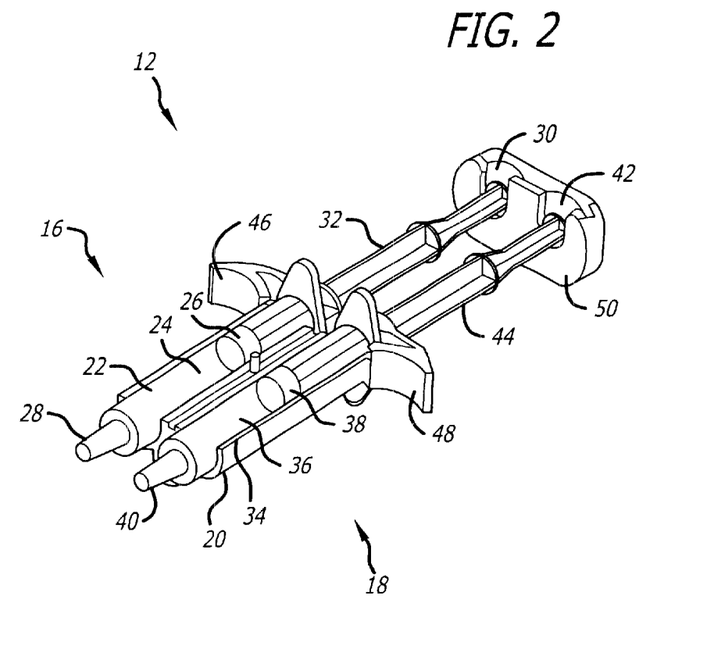
FIG. 2 is an elevated sectional view of the multi-syringe of the present invention.

As seen in FIG. 2, the multi-syringe applicator 12 disposes at least a first syringe device 16 and a second syringe device 18 coupled by a syringe coupler 20. It should be understood that the multi-syringe applicator 12 of the present invention may dispose a plurality of syringe devices, and the present embodiment should not be construed as limiting.

The first syringe device 16 comprises a first syringe container 22 storing a first component 24 and a first syringe piston 26, positionable within the first syringe container 22. The first syringe device 16 has a first syringe dispensing tip 28 connected to the first syringe container 22 extending beyond the syringe coupler 20, which may be coupled to a spray dispensing tip (not shown), and a proximal portion disposing a first syringe pusher 30, which is attached to the first piston rod 32.

Likewise, second syringe device 18 comprises a second syringe container 34 storing a second component 36 and a second syringe piston 38, positionable within the second syringe container 34. The second syringe device 18 has a second syringe dispensing tip 40 connected to the second syringe container 34 extending beyond the syringe coupler 20, and a proximal portion disposing a second syringe pusher 42, which is attached to the second piston rod 44.

As shown in FIG. 2, the syringe coupler 20 disposes at least two stationary stabilizers 46 and 48. In addition, FIG. 2 shows an actuation sleeve 50 attached to first syringe pusher 30 and second syringe pusher 42. Although not required for the operation of the present invention, the actuation sleeve 50 enhances the even disbursement of components 24 and 36 from the multi-syringe applicator 12.

To dispense the components 24 and 36, the at least two stationary stabilizers 46 and 48 are secured while equal pressure, directed from the proximal portion to the distal portion, is applied to the first syringe pusher 30 and second syringe pusher 42, resulting in first syringe piston 26 and second syringe piston 38 simultaneously progressing into first syringe container 22 and second syringe container 34, respectively. Thereafter, equal quantities of first component 24 and second component 36 are forcibly dispensed from the first syringe dispensing tip 28 and the second syringe dispensing tip 40.

Figure 3:
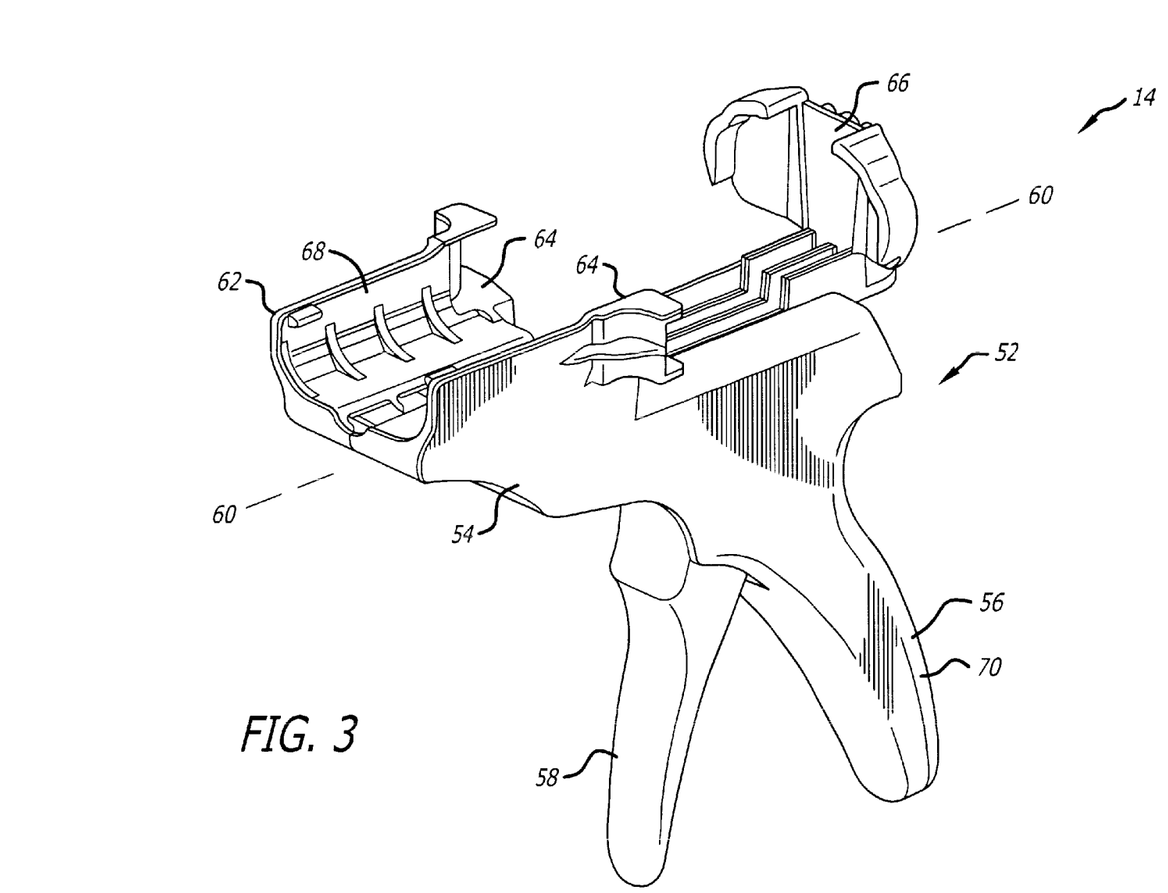
FIG. 3 is an elevated view of the handheld applicator of the present invention.

FIG. 3 shows the handheld applicator 14 for applying a medically useful multiple component material of the present invention. The applicator 14 comprises an applicator housing 52 having an elongated body 54 with a stationary handle 56 and a movable trigger handle 58.

As shown in FIG. 3, the elongated body 54 has a longitudinal axis 60, a distal portion 62, a medial portion disposing a stabilizer receiver 64, and a proximal portion which disposes a pushing interface 66 engageable with the first syringe pusher 30 and second syringe pusher 42, or the actuation sleeve 50, and further defines an interface cavity 68 for receiving the multi-syringe applicator 12 described above. The integral stationary handle 56 has a grip portion 70 thereby forming a pistol-type grip. The movable trigger device 58 is pivotally connected by trigger pin (not shown) to the applicator housing 52 adjacent to the grip portion 70 of the stationary handle 56.

Figure 4:
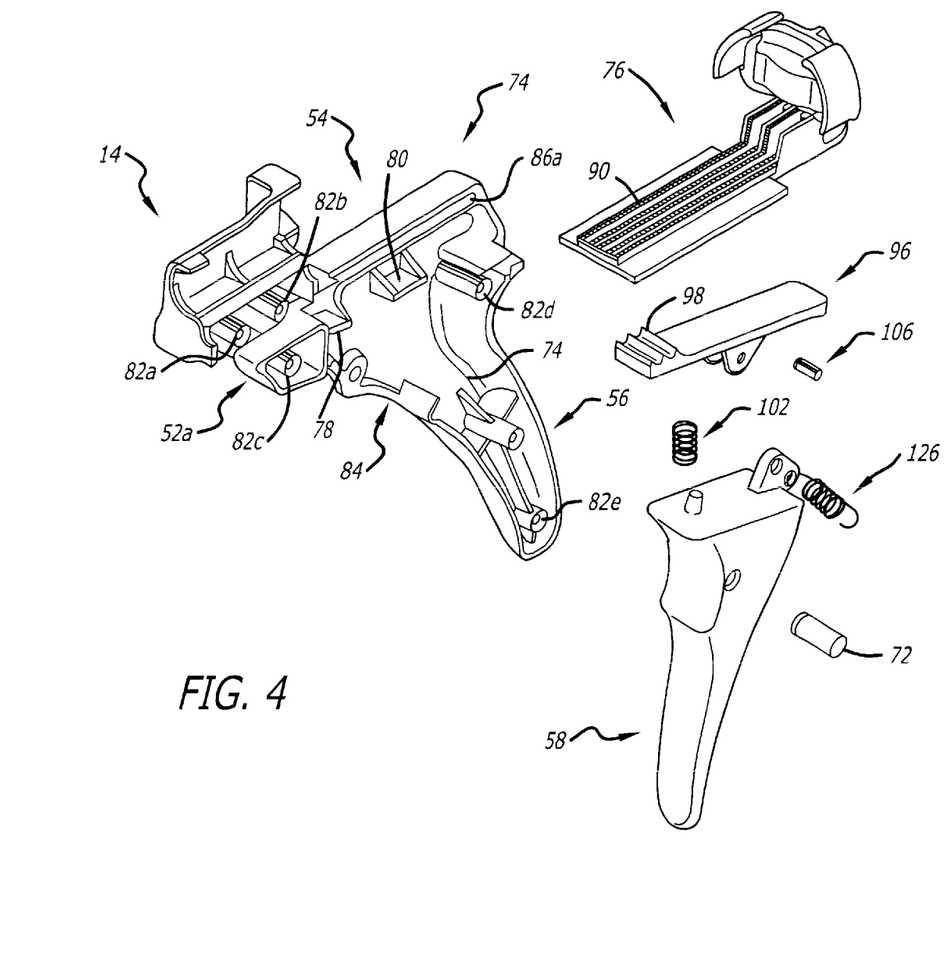
FIG. 4 is an elevated exploded view of the handheld applicator of the present invention.
Figure 4A:
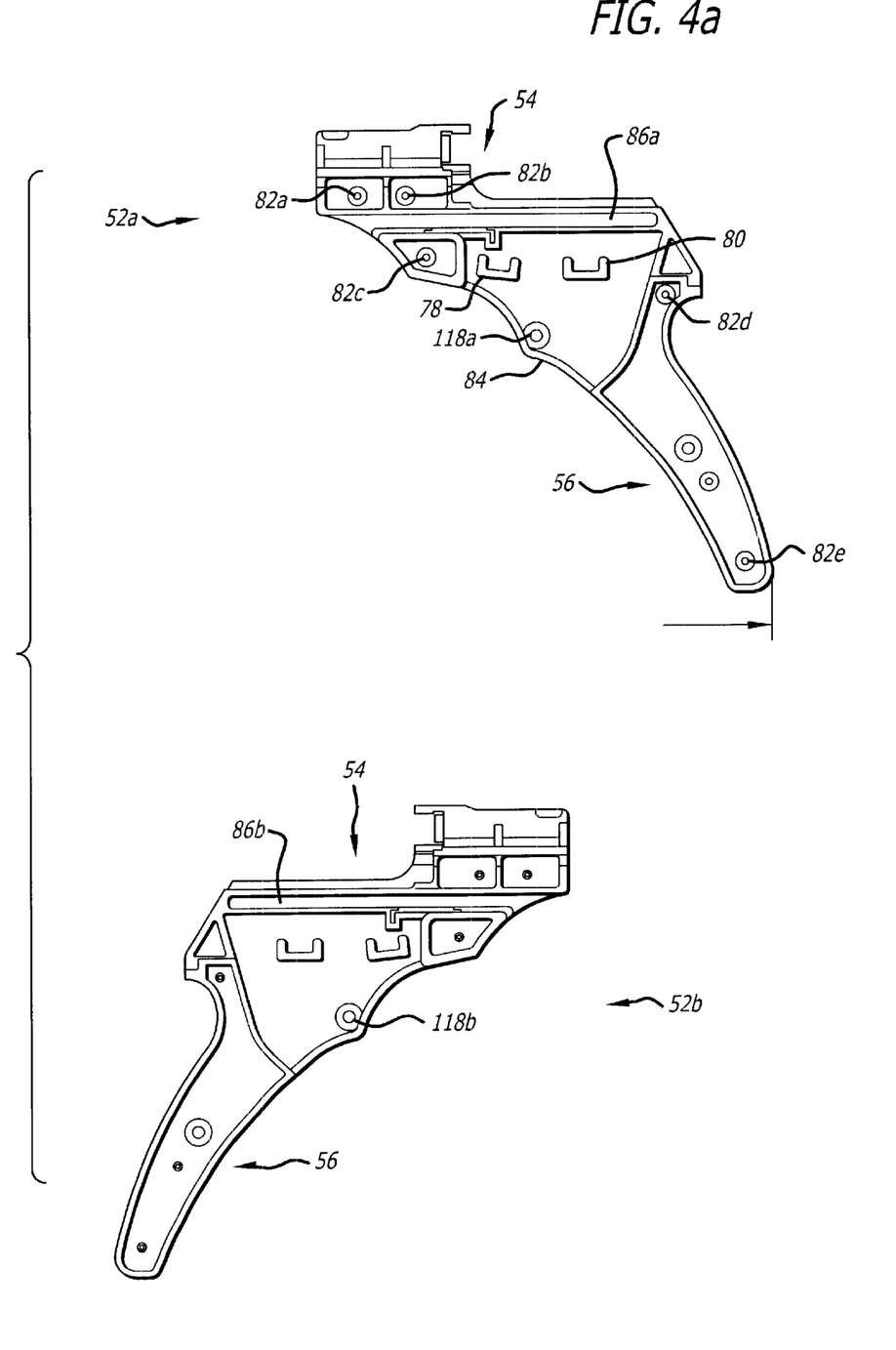
FIG. 4a is a side sectional view of the handheld applicator of the present invention.

FIGS. 4 and 4a show the internal components of the handheld applicator 14, which includes an applicator housing 52, an elongated body 54, a stationary handle 56, and a movable trigger device 58.

Figure 4B:
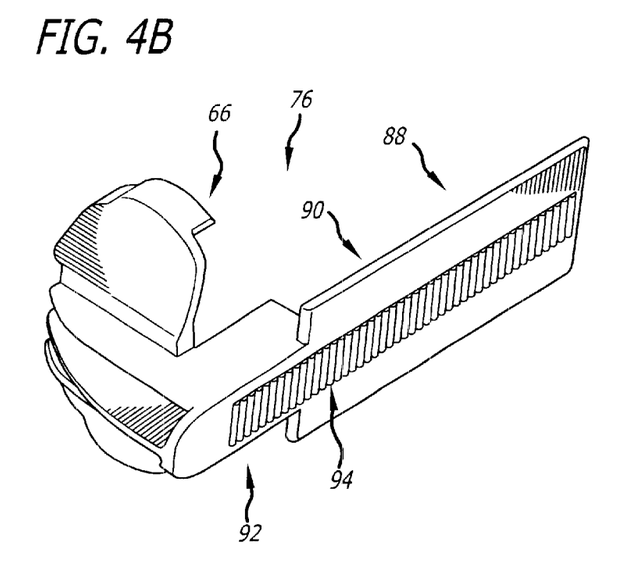
FIG. 4b is a side elevated view of the bottom of the engagement member of the present invention.

As seen in FIGS. 4 and 4a the applicator housing 52 may be formed of separable halves, for example applicator housing first half 52a and applicator housing second half 52b. These halves, when assembled, define an applicator cavity 74, which houses the drive assembly 76, return stop 78, dispensing stop 80, assembly ports 82a–82e, and trigger receiving port 84. The drive assembly 76 advances within advancement tracks 86a and 86b formed within applicator housing halves 52a and 52b. As shown in FIGS. 4 and 4b, the drive assembly 76 comprises a engagement member 88, attached to the pushing interface 66, having an exterior first surface comprising a exterior tray 90 and an internal second surface comprising an drive track 92. The drive track 92 features a series of drive teeth 94 disposed within the applicator cavity 74. The degree of dispensing control may be enhanced by increasing the frequency of teeth disposed on drive track 92.

Figure 4C:
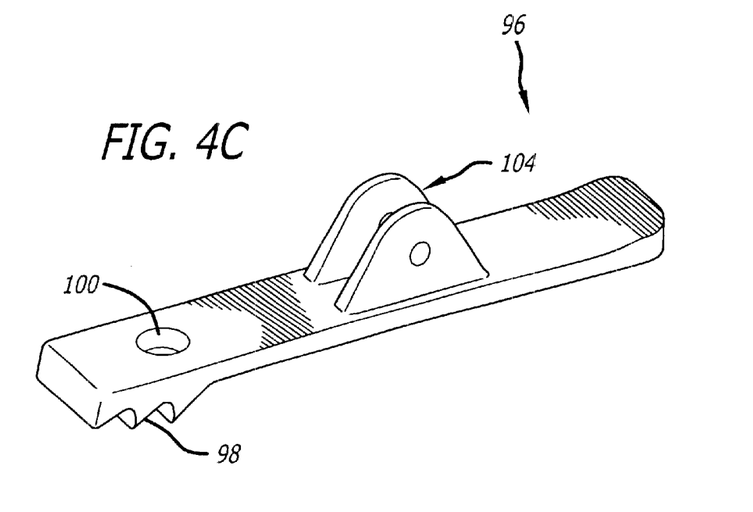
FIG. 4c is a side elevated view of the bottom of the movement actuator of the present invention

Referring to FIGS. 4 and 4c, disposed proximate the drive track 92 is a movement actuator 96 having a first surface disposing movement teeth 98, which engage the drive teeth 94 disposed on the engagement member 88, and a second surface disposing a biasing device receiver 100, which securely receives a biasing member 102, and an attachment interface 104, which pivotally attaches the movement actuator 96 to the moveable trigger device 58 with an attachment pin 106. FIGS. 4 and 4c illustrate the first surface and second surface of the movement actuator 96. As seen in FIG. 4, a proximal portion of the movement actuator 96 extends beyond the proximal portion of the elongated body 54, and may be operated by the user.

Figure 5:
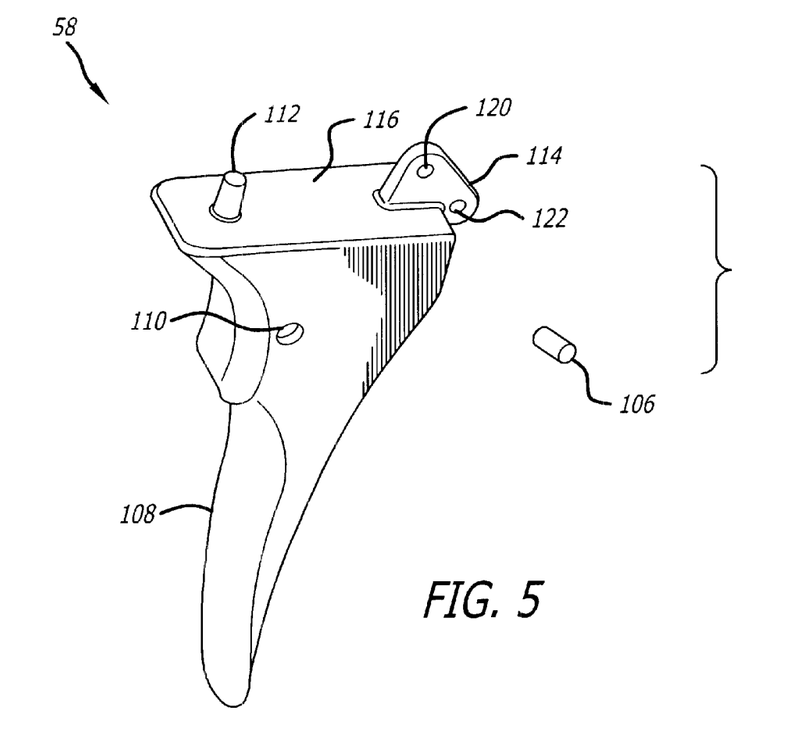
FIG. 5 is a side elevated view of the moveable trigger device of the present invention.

FIG. 5 shows the moveable trigger device 58 of the present invention. The moveable trigger device 58 features a contoured gripping surface 108, a trigger mounting port 110, a biasing member mount 112, and an actuator mount 114 disposed on the interface surface 116. The moveable trigger device 58 provides an actuatable member for dispensing the components while providing a tactile response of component deposition to the operator. It is within the scope of the present invention to provide alternative deposition response mechanisms including, without limitation, audible alerts and visual alerts.

The contoured gripping surface 108 permits the operator to easily grasp and actuate the device. The trigger mounting port 110 receives a trigger pivot pin 72 (See FIG. 4) and pivotally attaches the moveable trigger device 58 to trigger mounts 118a and 118b located on the applicator housing 52a and 52b. It should be noted that the pivoting motion of the moveable trigger device 58 disclosed herein should not be construed as limiting. The moveable trigger device 58 may be adapted to utilize a sliding motion or a similar motion.

Disposed on the interface surface 116 is the biasing member mount 112, to retain and position a biasing member 102. The biasing member 102 may include, for example, a coiled spring or leaf spring. When the device is assembled, the biasing member 102 forcibly biases the movement teeth 98 on the movement actuator 96 to engage the drive teeth 94 disposed on the engagement member 88.

In a relaxed state, the interface surface 116 contacts the return stop 78 thereby limiting the mechanical force the handheld applicator 14 can apply to the multi-syringe applicator 12. When dispensing material, the interface surface 116 contacts the dispensing stop 80 as the moveable trigger device 58 is moved towards the stationary handle 56, thereby limiting dispensing stroke length and the quantity of material dispensed during one operation cycle.

As seen in FIGS. 4 and 5, the actuator mount 114, located on interface surface 116, disposes a movement actuator mount 120 and a trigger biasing member mount 122. The movement actuator mount 120 pivotally attaches the movement actuator 96 to the moveable trigger device 58 with an actuator pin 106. The trigger biasing member mount 122 is connected to a trigger biasing member 126 which is attached to the biasing anchor 128 formed within the stationary handle 56. The trigger biasing member forces the interface surface 116 to contact the return stop 78 in a relaxed state.

Figure 6:
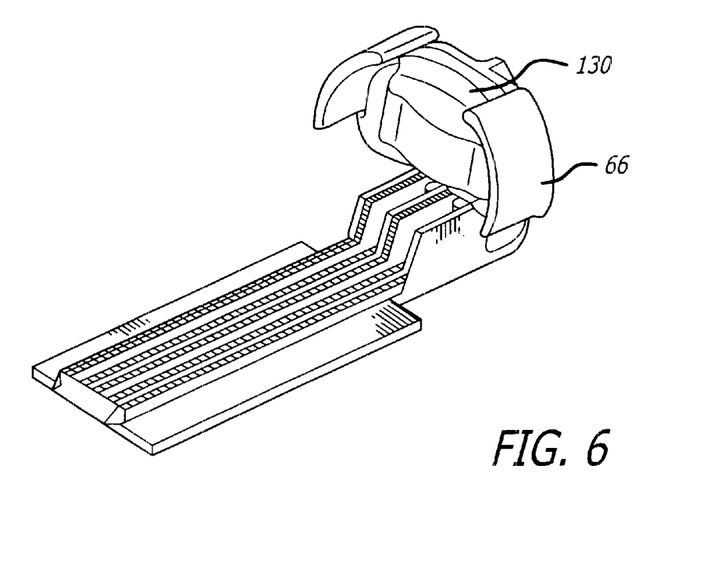
FIG. 6 is a side elevated view of the force dampener attached to the pushing member of the present invention.
Figure 6A:
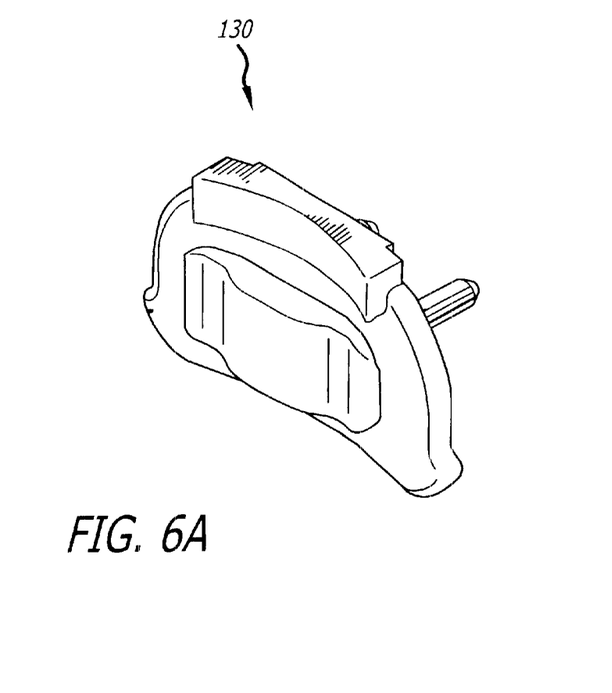
FIG. 6a is a side elevated view of the force dampener of the present invention.

An additional embodiment of the present invention is illustrated in FIGS. 6 and 6a. A force dampener 130 is positioned on the pushing interface 66 so as to contact the first syringe pusher 30 and the second syringe pusher 42, or alternatively the actuation sleeve 50. The force dampener 130 limits the amount of kinetic energy exerted on the syringe pistons at any given instant, storing the force moment as potential energy within the force dampener 130. Furthermore, the force dampener 130 is particularly useful in regulating the force initially applied to the multi-syringe applicator 12 by the handheld applicator 14 during operation. The force dampener 130 may be constructed of a plurality of materials, for example, an elastomer, and may be affixed to the pushing interface 66 in a variety of ways, including adhesively affixed and mechanically affixed. Additionally, the force dampener 130 may be removed from the pushing interface 66 by the operator should the need arise.

Figure 7:
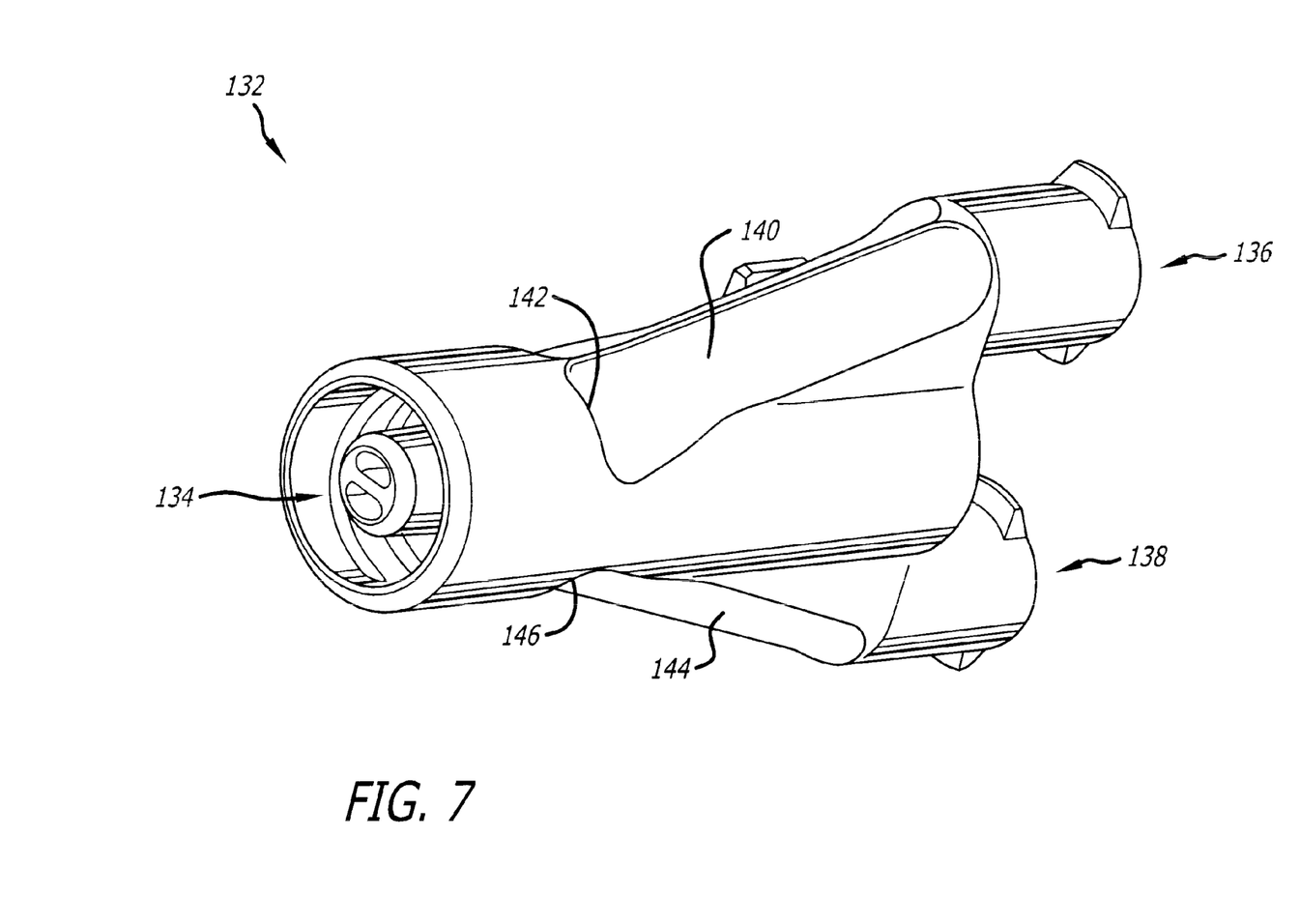
FIG. 7 is a side elevated view of a spray dispensing tip of the present invention.

FIG. 7 shows another embodiment of the present invention which includes the addition of a spray dispensing tip 132, comprising a distal portion having a component mixing device 134 and a proximal portion disposing at least a first syringe receiver 136 and at least a second syringe receiver 138. A first component channel 140, having a first channel outlet 142 terminating at the component mixing device 134, is connected to the first syringe receiver 136. Similarly, a second component channel 144, having a second channel outlet 146 terminating at the component mixing device 134, is connected to the second syringe receiver 138. The component mixing device 134 accepts component material from the first channel outlet 142 and second channel outlet 146 simultaneously, thereby mixing the components. The component mixing device 134 atomizes the mixed material and dispenses the mixture in droplet form. The spray dispensing tip 132 may couple directly to the dispensing tips of first and second syringes, or alternatively may attach to the handheld applicator 14 in a slidable relation, slip-fit relation, or other mechanical fashion. Alternatively, a plurality of dispensing devices could be attached to the apparatus 10 including, without limitation, cannulas and catheters.

In an additional embodiment of the present invention, an advancement regulator (not shown) may be positioned within the at least one of the advancement tracks 86a or 86b, or both. The advancement regulator (not shown) may comprise a leaf spring positioned along the longitudinal axis of the advancement track 86a or 86b, or both, and assists in providing smooth advancement of the engagement member 88 within the tracks.

The present invention also discloses a method of using a handheld multi-syringe applicator to apply a multiple component fluid. To operate the apparatus 10 a multi-syringe applicator 12 is positioned within the interface cavity 68 such that the first syringe pusher 30 and second syringe pusher 42, or alternatively actuation sleeve 50, contact the pushing interface 66, and stabilizers 46 and 48 contact the stabilizer receiver 64.

The handheld applicator 14 is held by the operator such that the operator's fingers contact the contoured gripping surface 108 of the moveable trigger device 58 and the palm portion of the operator's hand contacts the grip portion of the stationary handle 56. Thereafter, the apparatus 10 is positioned proximate the area of interest.

Once positioned, the operator squeezes the moveable trigger device 58. The movement of the moveable trigger device 58 towards the stationary handle 56 results in the actuator mount 114 and movement actuator 96 to raise. This movement results in movement teeth 98 located on the movement actuator 96 to interface with the drive teeth 94 disposed on the drive track 92 located on the engagement member 88, thereby forcibly advancing the engagement member 88 along the longitudinal axis 60 of the elongated body 54. As the engagement member 88 is advanced, the longitudinal distance between the pushing interface 66 and the stabilizer receiver 64 is decreased, resulting in compressive force being applied to the multi-syringe applicator 12. Thereafter, the first component 24 and second component 36 are controllably dispensed from their respective containers.

As pressure is continually applied to the moveable trigger device 58, the interface surface 116 is raised to contact the dispensing stop 80. One full operational cycle comprises actuation of the moveable trigger device 58 such that contact between the interface surface 116 and the return stop 78 terminates and contact between the interface surface 116 and the dispensing stop 80 occurs. As those skilled in the art will appreciate the present invention permits the operator to controllably dispense varying amounts of material by ceasing the application of pressure to the moveable trigger device 58 prior to the interface surface 116 contacting the dispensing stop 80. With pressure no longer applied to the moveable trigger device 58, the trigger biasing member 122 forcibly returns the moveable trigger device 58 to a relaxed position, wherein the interface surface 116 contacts the return stop 78.

When the desired amount of material has been dispensed the operator may cease applying longitudinal pressure to the multi-syringe applicator 12 by the handheld applicator 14. To release this pressure the operator may forcibly move the exposed proximal portion of the movement actuator 96 towards the engagement member 88, thereby disengaging the movement teeth 98 from the drive teeth 92 located on the engagement member 88. The engagement member 88 may then be moved towards the proximal portion of the elongated body 54. Thereafter, the multi-syringe applicator 12 may be removed from the handheld applicator 14.

The present invention also discloses a method of eliminating or reducing the occurrence component failure when applying a multiple component fluid using a multi-syringe applicator 12 and a handheld applicator 14. Typically, multi-syringe applicators 12 are commonly single-use disposable devices constructed of inexpensive plastics and polymers. The application of force to the first piston rod 32 and second piston rod 44 of the multi-syringe applicator 12 will result in the application of the fluid components, while application of excessive force to the first piston rod 32 and the second piston rod 44 could result in component failure. When used alone, failure of a multi-syringe applicator 12 rarely occurs as the quantum of mechanical advantage obtainable is limited by the operator's physiology, in that force a human hand can apply is within the operational parameters of the multi-syringe applicator 12. The use of a handheld applicator 14 increases the obtainable mechanical advantage, thereby enabling the application of excessive force to the multi-syringe applicator 12. Therefore, the possibility of component failure is greatly increased.

The applicant has identified and addressed this problem in the present invention with a method of dispensing a medically useful fluid from a multi-syringe applicator 12 with a handheld applicator 14 with a reduced likelihood of component failure. The method includes coupling a multi-syringe applicator 12 to handheld applicator 14 as provided above. The operator may then apply force to the dispensing actuator, for example the moveable trigger device 58, to apply the medically useful material. As a result, force is applied to the multi-syringe applicator less than, equal to, or greater than the force applied dispensing actuator, thereby defining a mechanical advantage. The present invention discloses a mechanical advantage limiting device, for example a return stop 78 and a dispensing stop 80, to regulate the mechanical advantage obtained. It should be noted the present disclosure is not limiting, and alternative mechanical advantage limiting devices are contemplated, including audible alerts, visual alerts, piston advancement regulators, and various force dampening devices. Additionally, the use of a force dampener 130 may be used to limit the mechanical advantage.

In closing it is understood that the embodiments of the invention disclosed herein are illustrative of the principles of the invention. Other modifications may be employed which are within the scope of the invention; thus, by way of example but not of limitation, alternative moveable trigger devices, alternative dispensing tips including cannulas and catheters, and alternative multi-syringe applicator device. Accordingly, the present invention is not limited to that precisely as shown and described in the present invention.

What is claimed is:

1. A multi-component applicator for mixing and applying at least a first and a second component, comprising:
    a multi-syringe applicator comprising at least a first syringe container storing a first component therein, and having a first syringe piston connected to a first piston rod disposing a first pusher, and at least a second syringe container storing a second component therein, and having a second syringe piston connected to a second piston rod disposing a second pusher;
    a handheld applicator gun comprising an elongated body portion defining an applicator housing, a stationary handle portion, and a moveable trigger device;
    said moveable trigger device connected to said applicator housing and adjacent thereto;
    said moveable trigger device comprising a movement actuator connected to an advanceable engagement member, wherein actuation of said moveable trigger device advances said engagement member; and
    a return stop and a dispensing stop connected to said applicator housing and engageable with said moveable trigger device, said return stop and said dispensing stop configured to limit the mechanical advantage exertable by said handheld applicator on said multi-syringe applicator.

2. The device of claim 1, wherein said movement actuator further comprises a biasing member to lockably engage said engagement member with said movement actuator, thereby restricting movement of the engagement member.

3. The device of claim 2, wherein said biasing member may be disengaged by the operator, thereby permitting movement of the engagement member.

4. The device of claim 2, wherein said biasing member comprises a spring.

5. The device of claim 1, where said applicator housing further comprises an interface cavity capable of receiving said multi-syringe applicator.

6. The device of claim 5, wherein said interface cavity is capable of receiving a plurality of multi-syringe applicators.

7. The device of claim 1, wherein said engagement member further comprises a pushing interface.

8. The device of claim 7, wherein said pushing interface further comprises a force dampener.

9. The device of claim 8, wherein said force dampener is made of an elastomer.

10. The device of claim 8, wherein said force dampener is made of silicon.

11. The device of claim 1, wherein said return stop is positioned to contact said moveable trigger device, thereby limiting the stroke length of said moveable trigger device.

12. The device of claim 11, wherein said moveable trigger device further comprises a trigger biasing member, said trigger biasing member forcing said moveable trigger device to contact said return stop absent the application of pressure to said moveable trigger device.

13. The device of claim 12, wherein said trigger biasing member is a spring.

14. The device of claim 1, wherein said dispensing stop is positioned to contact said moveable trigger device, thereby limiting the quantity of said first component and second component dispensed at one time.

15. The device of claim 1, wherein said stationary handle forms a pistol-type grip.

16. The device of claim 1, wherein said applicator housing is capable of receiving a spray producing device, thereby enabling the sprayed application of said first and second components.

17. The device of claim 1 wherein said applicator housing further comprises an applicator cavity, said applicator cavity having said return stop located therein.

18. The device of claim 1 wherein said applicator housing further comprises an applicator cavity, said applicator cavity having said dispensing stop located therein.

19. The device of claim 1 wherein said applicator housing further comprises an applicator cavity, said applicator cavity having said return stop and said dispensing stop located therein.

20. A multi-component applicator for mixing and applying at least a first and a second component, comprising:
   a multi-syringe applicator comprising at least a first syringe container storing a first component therein, and having a first syringe piston connected to a first piston rod disposing a first pusher, and at least a second syringe container storing a second component therein, and having a second syringe piston connected to a second piston rod disposing a second pusher;
   a handheld applicator gun comprising an elongated body portion defining an applicator housing, a stationary handle portion, and a moveable trigger device;
   said moveable trigger device connected to said applicator housing and adjacent thereto;
   a movement actuator in communication with said moveable trigger device and connected to an advanceable engagement member, said advanceable engagement member comprising a pushing interface having a force dampener attached thereto,
   wherein actuation of said moveable trigger device advances said engagement member; and
   a return stop and a dispensing stop connected to said applicator housing and engageable with said moveable trigger device, thereby limiting the advancement stroke lengths of the first and said second pistons disposed in said first and second containers.

21. A method of optimizing the force applied by a hand held applicator, comprising:
   providing a handheld applicator capable of exerting increased force on a multi-component applicator coupled thereto, said handheld applicator providing a mechanical advantage in applying said force; and
   regulating the mechanical advantage of said handheld applicator to control the application of said force applied by said handheld applicator to said multi-component applicator.

22. The method of claim 21, wherein said regulation of said applied force is accomplished by a dispensing stop, thereby limiting the mechanical advantage obtained by said handheld applicator.

23. The method of claim 21, wherein said regulation of said applied force is accomplished by a return stop, thereby limiting the mechanical advantage obtained by said handheld applicator.

24. The method of claim 21, wherein said regulation of said applied force is accomplished by a dispensing stop and a return stop, thereby limiting the mechanical advantage obtained by said handheld applicator.

25. The method of claim 21, wherein said regulation of said applied force is accomplished by an audible alert.

26. The method of claim 21, wherein said regulation of said applied force is accomplished by a visual alert.

27. The method of claim 21, wherein regulation of said applied force is accomplished by a tactile alert.

28. The method of claim 21, wherein said regulation of said applied force is accomplished by a piston advancement regulator.

29. The method of claim 21, wherein said regulation of said applied force is accomplished by a force dampener.

30. A handheld multi-component applicator gun for mixing and applying at least a first and a second component, comprising:
   an elongated body portion capable of receiving a multi-syringe applicator, said body portion comprising a pushing interface engageable with the multi-syringe applicator;
   a drive assembly comprising an engagement member attached to said pushing interface, said engagement member having a first engagement member surface comprising an exterior tray and a second engagement member surface comprising a drive track having one or more teeth disposed thereon;
   a stationary handle portion; and
   a movable trigger device connected to said applicator housing and adjacent thereto, said movable trigger device comprising a movement actuator connected to said drive assembly, said movement actuator having an actuator surface comprising movement teeth engageable with said drive teeth.

31. The handheld multi-component applicator gun of claim 30 wherein said movement actuator has a proximal portion and said elongated body portion has a proximal portion, said proximal portion of said movement actuator extending beyond said proximal portion of said elongated body portion.

32. The handheld multi-component applicator gun of claim 30 wherein said elongated body portion defines an applicator cavity which houses said drive assembly, said elongated body portion further comprising advancement tracks within which said drive assembly advances.

33. A handheld multi-component applicator gun for mixing and applying at least a first and a second component, comprising:
   a multi-syringe applicator comprising at least a first syringe container storing a first component and having a first syringe piston connected to a first piston rod and having a first piston pusher attached thereto, and at least a second syringe container storing a second component therein and having a second syringe piston connected to a second piston rod and having a second piston pusher attached thereto;

an elongated body portion capable of receiving said multi-syringe applicator, said elongated body portion comprising a pushing interface engageable with the multi-syringe applicator;

a drive assembly comprising an engagement member attached to said pushing member, said engagement member having a first engagement member surface comprising an exterior tray and a second engagement member surface comprising a drive track having one or more drive teeth disposed thereon;

a stationary handle portion; and a movable trigger device connected to said applicator housing and adjacent thereto, said movable trigger device comprising a movement actuator connected to said drive assembly, said movement actuator having an actuator surface comprising movement teeth engageable with said drive teeth.

34. A device for regulating the mechanical advantage obtainable by a multi-syringe applicator having a movable trigger device in communication with a movement actuator, comprising:

a dispensing stop located within said applicator and configured to engage said movable trigger thereby restricting a range of dispensing motion obtainable by said moveable trigger device; and a return stop located within said applicator and configured to engage said movable trigger thereby restricting a range of actuation motion obtainable by said moveable trigger device.

35. A force transmission system used in multi-component applicators, comprising:

an applicator cavity;

a drive assembly having a first surface comprising an exterior tray and a pushing interface engageable with at least one syringe applicator and a second surface located within said applicator cavity and comprising a drive track having at least one drive tooth thereon; and an actuation assembly located within said applicator cavity and having an actuation device disposing a movement actuator thereon, said movement actuator having a distal portion having movement teeth engageable with said at least one drive tooth, said actuation assembly having a proximal portion disposing a disengagement member.

* * * * *